(12) United States Patent
Kono (10) Patent No.: US 12,004,962 B2
(45) Date of Patent: Jun. 11, 2024

(54) INTERBODY CAGE

(71) Applicant: Teijin Nakashima Medical Co., Ltd., Okayama (JP)

(72) Inventor: Mamoru Kono, Kobe (JP)

(73) Assignee: TEIJIN NAKASHIMA MEDICAL CO., LTD., Okayama (JP)

( * ) Notice: Subject to any disclaimer, the term of this patent is extended or adjusted under 35 U.S.C. 154(b) by 610 days.

(21) Appl. No.: 17/292,202

(22) PCT Filed: Oct. 28, 2019

(86) PCT No.: PCT/JP2019/042133
§ 371 (c)(1),
(2) Date: May 7, 2021

(87) PCT Pub. No.: WO2020/095745
PCT Pub. Date: May 14, 2020

(65) Prior Publication Data
US 2021/0386554 A1  Dec. 16, 2021

(30) Foreign Application Priority Data

Nov. 9, 2018 (JP) ................................ 2018-211147

(51) Int. Cl.
*A61F 2/44* (2006.01)
*A61F 2/30* (2006.01)

(52) U.S. Cl.
CPC .............. *A61F 2/447* (2013.01); *A61F 2/442* (2013.01); *A61F 2/4455* (2013.01); *A61F 2002/30398* (2013.01)

(58) Field of Classification Search
CPC ......... A61F 2/442; A61F 2/4455; A61F 2/447
See application file for complete search history.

(56) References Cited

U.S. PATENT DOCUMENTS 3,941,028 A * 3/1976 Lobello ................. F16B 13/066
411/75
5,554,191 A 9/1996 Lahille et al.
(Continued)

FOREIGN PATENT DOCUMENTS

| JP | 2669379 B2 | 10/1997 |
| KR | 10-0953930 B1 | 4/2010 |
| WO | 2006/078972 A2 | 7/2006 |

OTHER PUBLICATIONS

International Search Report for PCT/JP2019/042133 dated Jan. 21, 2020 [PCT/ISA/210].

(Continued)

*Primary Examiner* — Ellen C Hammond
(74) *Attorney, Agent, or Firm* — Sughrue Mion, PLLC (57) ABSTRACT

Provided is a structurally stable interbody cage. An interbody cage 1 includes a main body 2 distally including two branches 20,21 that are spaced apart from each other upward and downward, a rod 3 provided in the main body 2 so as to extend between the two branches 20,21, and a slider 4 configured to separate the two branches 20,21 upward and downward, the slider 4 being supported by the rod 3 so as to be movable in an axis direction of the rod, wherein the two branches 20,21 each distally have an inclined surface 26A, the inclined surfaces 26A facing each other, the distance between the inclined surfaces 26A gradually increasing toward distal ends thereof; the slider 4 slides on the inclined surfaces 26A of the two branches 20,21 when the slider 4 moves in the axis direction of the rod 3, and the two branches 20,21 each proximally have a constricted part 27 with a narrow thickness and an opening 5 is present between the upper constricted part 27 and the lower constricted part 27, the opening 5 being formed by a plurality of holes 50 to 52 continuous in the axis direction of the rod 3 and having (Continued)

an upper edge and lower edge that form protruding curves in a lateral view.

7 Claims, 12 Drawing Sheets

(56) References Cited

U.S. PATENT DOCUMENTS

| | | | | |
|---|---|---|---|---|
| 6,821,298 | B1* | 11/2004 | Jackson | A61F 2/4455 623/17.11 |
| 7,655,046 | B2* | 2/2010 | Dryer | A61F 2/446 623/17.11 |
| 9,125,701 | B2* | 9/2015 | Pech | A61B 17/68 |
| 9,579,213 | B2* | 2/2017 | Bal | A61F 2/442 |
| 10,039,650 | B2* | 8/2018 | Lamborne | A61F 2/447 |
| 10,842,644 | B2* | 11/2020 | Weiman | A61F 2/447 |
| 2002/0045945 | A1* | 4/2002 | Liu | A61F 2/4611 623/17.16 |
| 2006/0030943 | A1 | 2/2006 | Peterman | |

OTHER PUBLICATIONS

Written Opinion for PCT/JP2019/042133 dated Jan. 21, 2020 [PCT/ISA/237].
Office Action for corresponding JP Application No. 2018-211147 dated Sep. 8, 2020.

* cited by examiner

INTERBODY CAGE

CROSS REFERENCE TO RELATED APPLICATIONS

This application is a National Stage of International Application No. PCT/JP2019/042133 filed Oct. 28, 2019, claiming priority based on Japanese Patent Application No. 2018-211147 filed Nov. 9, 2018.

TECHNICAL FIELD

The present invention relates to an interbody cage configured to be attached between two vertically adjacent vertebral bodies of the spine as an implant in the surgery of spine diseases, such as lumbar spinal stenosis, spondylolisthesis, and spinal disc herniation.

BACKGROUND ART

In the surgery of spine diseases, spinal fusion has been performed by attaching an interbody cage between two vertically adjacent vertebral bodies of the spine to reinforce the intervertebral bodies, while stably maintaining the space between the intervertebral bodies in a near-normal condition.

PTL 1 discloses an expandable interbody cage. The interbody cage of PTL 1 includes a main body having two branches that are separated upward and downward by a slit, a screw provided in the main body so as to extend along the slit, and a cylindrical roller into which the screw is screwed. In the interbody cage of PTL 1, the roller is moved with the rotation of the screw in the direction of the axis of the screw. At this time, the roller slides on the distally positioned oblique baring surface of each branch to push the branches upward or downward, thereby separating the branches from each other and expanding the interbody cage. Each branch proximally has an opening that is connected to the slit. Due to the vertically large space of the opening, each branch proximally has a constricted part with a narrow thickness. This constricted part allows each branch to flexibly bend and deform when the branch deforms to separate from the other branch with the movement of the roller.

The lordosis angle of the spine varies from person to person, and depending on the site. Thus, an interbody can be reinforced with an interbody cage in a condition suitable for a patient by adjusting the degree of expansion of the interbody cage according to the height and angle between the vertebral bodies to which the interbody cage is attached.

CITATION LIST

Patent Literature

PTL 1: U.S. Pat. No. 2,669,379

SUMMARY OF INVENTION

Technical Problem

When each branch is bent and deformed with the movement of the roller, a high stress is generated in the constricted part of each branch in the interbody cage disclosed in PTL 1. The constricted part of each branch is weak due to the narrow and thin thickness configured to allow each branch to easily open upward and downward. Thus, when stress increases locally in the constricted parts, forming stress concentration, the constricted parts become susceptible to breakage. Because the shape of the opening of the interbody cage disclosed in PTL 1 allows stress to locally concentrate at the constricted part of each branch, the interbody cage of PTL 1 is structurally unstable, leaving room for improvement in this regard.

The present invention was made to solve the above problem. An object of the present invention is to provide a structurally stable interbody cage.

Solution to Problem

A feature of the interbody cage according to the present invention is that the interbody cage is configured to be attached between adjacent vertebral bodies of a spine, the interbody cage comprising
- a main body distally including a pair of branches, the branches being spaced apart from each other upward and downward,
- a rod provided in the main body so as to extend between the two branches, and
- a slider configured to separate the two branches upward and downward, the slider being supported by the rod so as to be movable in an axis direction of the rod, wherein
- the two branches each distally have an inclined surface, the inclined surfaces facing each other, a distance between the inclined surfaces gradually increasing toward distal ends thereof,
- the slider slides on the inclined surfaces of the two branches when the slider moves in the axis direction of the rod, and
- the two branches each proximally have a constricted part with a narrow thickness, and an opening is present between an upper constricted part and a lower constricted part, the opening being formed of a plurality of holes continuous in the axis direction of the rod and having an upper edge and lower edge that form protruding curves in a lateral view.

In a preferable embodiment of the interbody cage according to the present invention, the slider includes two contact surfaces that individually correspond to the respective inclined surfaces of the two branches, and each contact surface slides on the corresponding inclined surface when the slider moves in the axis direction of the rod.

In a preferable embodiment of the interbody cage according to the present invention, each contact surface comes in surface-to-surface contact with the corresponding inclined surface when the two branches receive pressure from the upper and lower vertebral bodies.

In a preferable embodiment of the interbody cage according to the present invention, a most proximal hole among the plurality of holes has a shape that is part of an ellipse long in the axis direction of the rod.

In a preferable embodiment of the interbody cage according to the present invention, the protruding curves of the plurality of holes have a radius of curvature that is smaller toward the distal end.

In a preferable embodiment of the interbody cage according to the present invention, the opening is flared so as to expand upward and downward toward the distal end in a lateral view.

In a preferable embodiment of the interbody cage according to the present invention, the main body and the slider are formed from a biocompatible material.

Advantageous Effects of Invention

In the interbody cage according to the present invention, the slider slides on the inclined surface of each branch of the main body by moving in the axis direction of the rod to push the inclined surfaces upward or downward. This causes each branch to deform such that the branches distally open upward and downward, separating the branches one above the other, and thereby expanding the interbody cage. Because the interbody can be adjusted to a normal height and angle by adjusting the degree of expansion of the interbody cage according to the patient, the spine can be corrected suitably for the patient (recovery and acquisition of a lordosis angle). Additionally, the interbody cage reliably reinforces the interbody and prevents the interbody from being squished by the pressure applied from the upper and lower vertebral bodies, making it possible to prevent delayed bone fusion and nonunion.

When each branch is bent and deformed with the movement of the slider, a high stress is generated at the constricted part of each branch, and this stress is likely to concentrate at the area near the proximal end position of the opening. However, due to the opening formed by connecting a plurality of holes, the interbody cage according to the present invention enables the stress that concentrates at a hole corresponding to the proximal end position of the opening to be dispersed into the adjacent hole to reduce the stress concentration at the hole corresponding to the proximal end position of the opening. Thus, the interbody cage according to the present invention decreases the maximum stress generated in the constricted part of each branch, and prevents well the breakage of the constricted part. Accordingly, the present invention provides a structurally stable interbody cage.

DESCRIPTION OF EMBODIMENTS

An embodiment of the present invention is described below with reference to the enclosed drawings. The interbody cage according to the present invention is attached in a space between two vertically adjacent vertebral bodies of vertebrae of the spine as an implant in the surgery of spine diseases, such as lumbar spinal stenosis, spondylolisthesis, and spinal disc herniation, to reinforce the interbody such that the interbody is stably maintained at a near-normal height and angle, for the purpose of correcting the spine or promoting bone union with a grafted bone.

FIGS. 1 to 7 illustrate an interbody cage 1 according to the embodiment. The interbody cage 1 includes a main body 2 distally including a pair of branches 20,21, a rod 3 built in the main body 2, and a slider 4 distally supported by the rod 3 so as to be movable in the axis direction. Note that in the following description, the longitudinal direction of the interbody cage 1 with a longitudinal shape is defined as follows; where the slider 4 is placed is the front side (distal end side), and the other side (the side on which a base 22 of the main body 2 is located) is the rear side (proximal end side).

The main body 2 is formed from a biocompatible material. Preferable examples of biocompatible materials include, for the main body 2 to have excellent durability, metallic materials, such as titanium, titanium alloy, and stainless steel, and plastic materials, such as polyether ether ketone (PEEK), polypropylene (PP), and polyethylene terephthalate (PET). In particular, PEEK is the most preferable example, from the standpoint of the excellent visibility of bone union in diagnostic imaging after surgery. PEEK also has an elasticity (hardness) substantially equivalent to that of bone. Thus, when the interbody cage 1 receives pressure from the upper and lower vertebral bodies with the interbody cage 1 attached between the vertebral bodies, the use of PEEK can prevent the interbody cage 1 from sinking into the vertebral bodies, and compressing nerves.

As illustrated in FIGS. 8 to 13, in addition to FIGS. 1 to 7, the main body 2 has a substantially U-shaped structure including the pair of branches 20,21 that extends in the longitudinal direction and the base 22 that connects the two branches 20,21. The base 22 includes a recess 23 that has a circular shape in a cross-sectional view with a bottom, and that extends in the longitudinal direction due to counterboring performed on the rear end surface. A head 30 of the rod 3 is rotatably placed into the recess 23. On the bottom of the recess 23, an insertion hole 24 into which a rod-shaped part 31 of the rod 3 passes through is formed. Because the insertion hole 24 has an outline smaller than that of the head 30 of the rod 3, the head 30 of the rod 3 hits the bottom of the recess 23 without passing through the insertion hole 24.

The two branches 20,21 are provided one above the other, with a space between the branches. The two branches 20,21 are integral in their proximal end (rear end) with the base 22, and are deformable so as to open upward and downward at their extremity (the end of the front side).

The two branches 20,21 each distally include a tapered part 25 whose thickness gradually decreases toward their extremity. The inner surface of the tapered part 25 (the lower surface of the branch 20 and the upper surface of the branch 21) has an inclined surface 26A that is linearly inclined in a cross-sectional view. The inclined surface 26A of the branch 20 and the inclined surface 26A of branch 21 face each other, and gradually increase the distance between them toward their extremity, forming a V shape. The inclination angle of the inclined surface 26A of each branch 20,21 is preferably 15° or more and 35° or less, and more preferably 20° or more and 30° or less with respect to a plain surface 26B adjacent to the inclined surface 26A on the rear side.

The two branches 20,21 each include a pair of guide walls 28 on their side edges in the width direction of the tapered part 25 (the side edges on the right and left). Both guide walls 28 are placed adjacent to the right and left sides of a separator 42 of the slider 4 so as to sandwich the separator 42. Both guide walls 28 function as a guide so that the slider 4 moves straight in the axis direction of the rod 3 without revolving in the circumferential direction of the rod 3, while moving in the axis direction.

The outer surfaces of the two branches 20,21 (the upper surface of the branch 20 and the lower surface of the branch 21) are substantially parallel to each other, and have an arch shape such that the center portion in the longitudinal direction curves by outwardly protruding. On the outer surfaces of the two branches 20,21, a plurality of projections 29 are provided separate apart in a serrated pattern in the longitudinal direction. The plurality of projections 29 engage with the upper and lower vertebral bodies or the intervertebral disc when the interbody cage 1 is attached between the vertebral bodies, and anchors the interbody cage 1 in the space between the vertebral bodies.

The two branches 20,21 have an orifice 53 formed in the center of the width direction, passing through in the vertical direction. The orifice 53 accommodates fragments of grafted bone for smoothly performing bone repair in the interbody, and has a shape perforated long in the longitudinal direction of each of the branches 20,21.

The rod 3 is formed from a biocompatible material. Preferable examples of biocompatible materials include, for the main body 2 to have excellent durability, metallic materials, such as titanium, titanium alloy, and stainless steel, and plastic materials, such as polyether ether ketone (PEEK), polypropylene (PP), and polyethylene terephthalate (PET). In particular, titanium alloy is the most preferable example.

Figure 14:
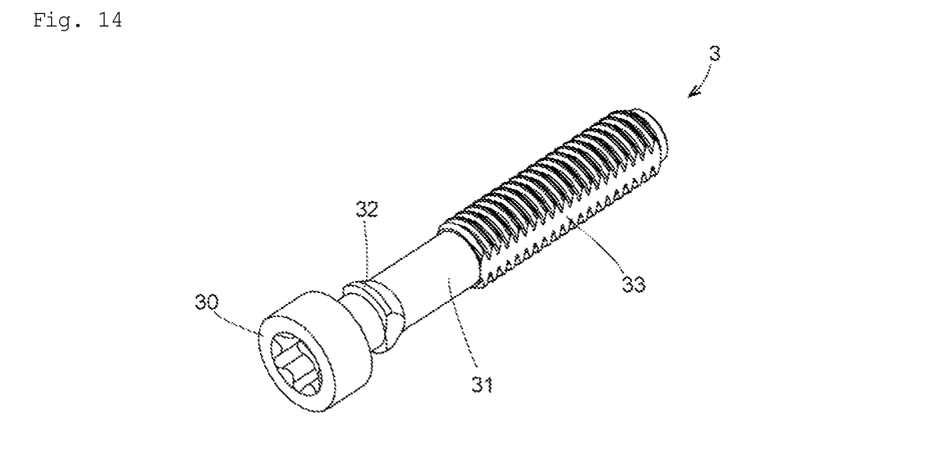
FIG. 14 is a perspective view of the rod.
Figure 15:
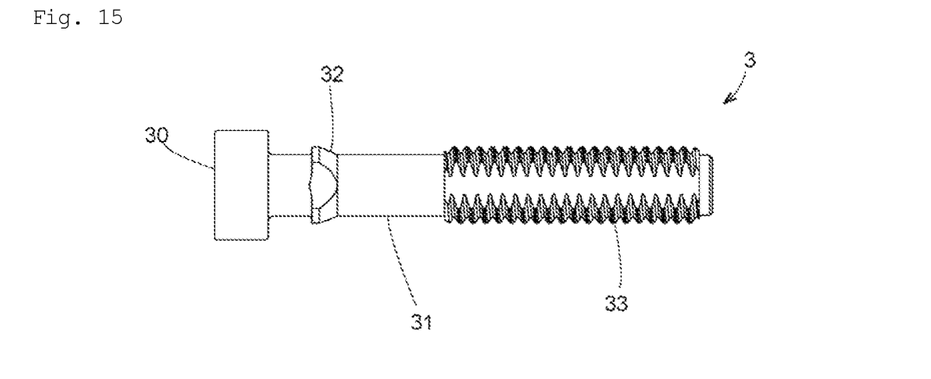
FIG. 15 is a lateral view of the rod.
Figure 16:
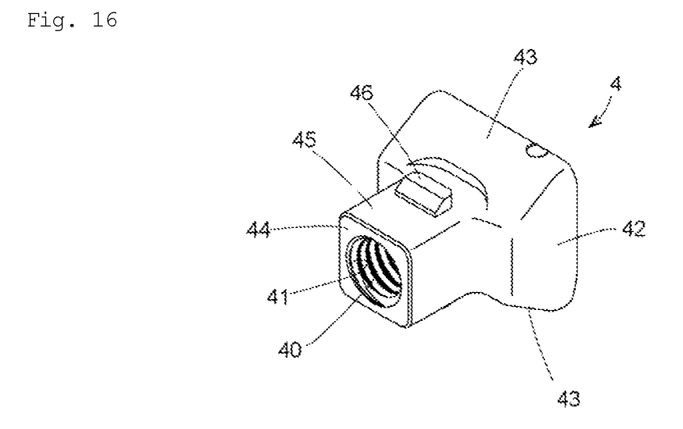
FIG. 16 is a perspective view of the slider.
Figure 17:
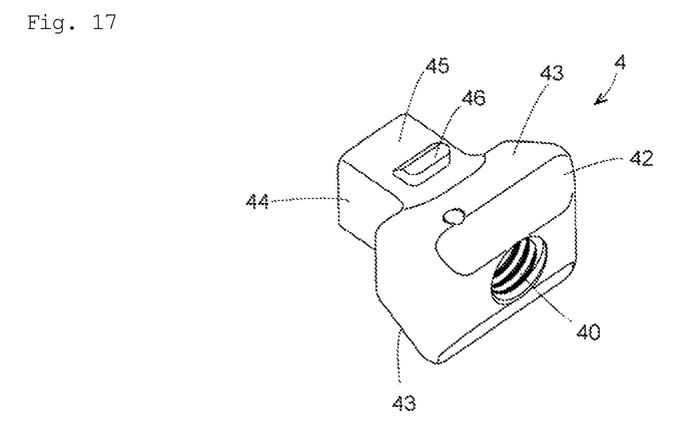
FIG. 17 is a perspective view of the slider.
Figure 18:
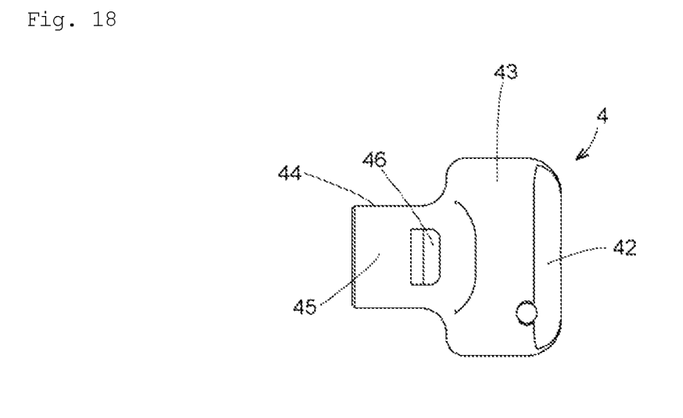
FIG. 18 is a plan view of the slider.
Figure 19:
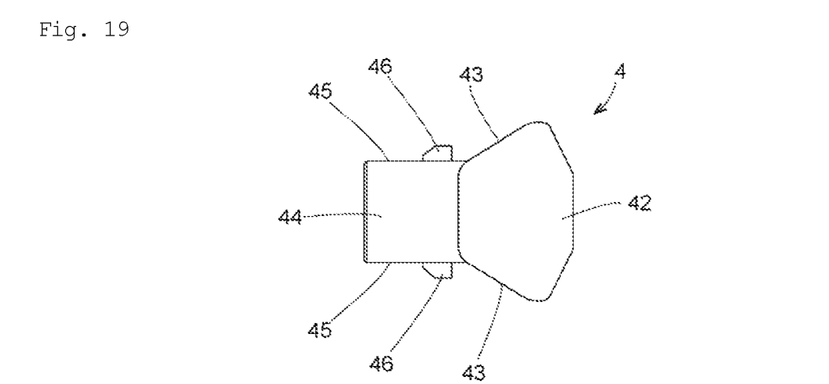
FIG. 19 is a lateral view of the slider.

As illustrated in FIGS. 14 and 15, in addition to FIGS. 1 to 7, the rod 3 is provided in the main body 2 so as to extend between the branches 20,21 in the longitudinal direction. The axis direction of the rod 3 is the same as the longitudinal direction of the branches 20,21. In this embodiment, a bolt is used for the rod 3. For example, the rod 3 includes the head 30 having a hexagonal hole, the rod-shaped part 31 protruding from the head 30, and a flange 32 proximally provided to the rod-shaped part 31 at a predetermined space from the head 30.

The head 30 is supported in the recess 23 of the base 22 in the main body 2. The rod-shaped part 31 protrudes between the two branches 20,21 of the main body 2, and extends between the branches 20,21 to the portion near the extremity. An external thread 33 that is screwed into an internal thread 41 of the slider 4, described later, is formed distally on the outer peripheral surface of the rod-shaped part 31. The flange 32 functions as a stopper by sandwiching the bottom of the recess 23 with the head 30 to regulate the movement of the rod 3 in the axis direction.

The slider 4 is formed from a biocompatible material. Preferable examples of biocompatible materials include, for the slider 4 to have excellent durability, metallic materials, such as titanium, titanium alloy, and stainless steel, and plastic materials, such as polyether ether ketone (PEEK), polypropylene (PP), and polyethylene terephthalate (PET). In particular, PEEK is the most preferable example, from the standpoint of excellent visibility of bone union in diagnostic imaging after surgery and the elasticity of PEEK, which is similar to that of bone.

As illustrated in FIGS. 16 to 19, in addition to FIGS. 1 to 7, the slider 4 has a through hole 40 formed from the rear end surface through the front end surface inside thereof. On the inner wall surface that forms the through hole 40, the internal thread 41 is formed. Screwing the external thread 33 of the rod 3 into this internal thread 41 enables the slider 4 to be supported by the rod 3, and the rotation of the rod 3 pushes the external thread 33 inward. This enables the slider 4 to move toward the proximal end (toward the head 30) in the axis direction of the rod 3.

The slider 4 includes a separator 42 configured to separate the two branches 20,21 of the main body 2 one above the other by moving toward the proximal end in the axis direction of the rod 3. The separator 42 has a substantially isosceles trapezoidal shape in a cross-sectional view, and includes two contact surfaces 43 one above the other at the positions that correspond to the inclined sides of the substantially isosceles trapezoid, such that the two contact surfaces 43 correspond to the respective inclined surfaces 26A of the two branches 20,21.

The contact surfaces 43 are each linearly inclined in a cross-sectional view and have a V-shape, gradually separating away from each other toward the front end surface of the slider 4. The inclination angle of each contact surface 43 is larger and steeper than the inclination angle of the corresponding inclined surface 26A. Specifically, the inclination angle of each contact surface 43 is preferably 20° or more and 40° or less, and more preferably 25° or more and 35° or less with respect to upper and lower plain surfaces 45 of an axis part 44 that is adjacent to the contact surfaces 43 and continuous with the rear end of the separator 42.

Figure 20:
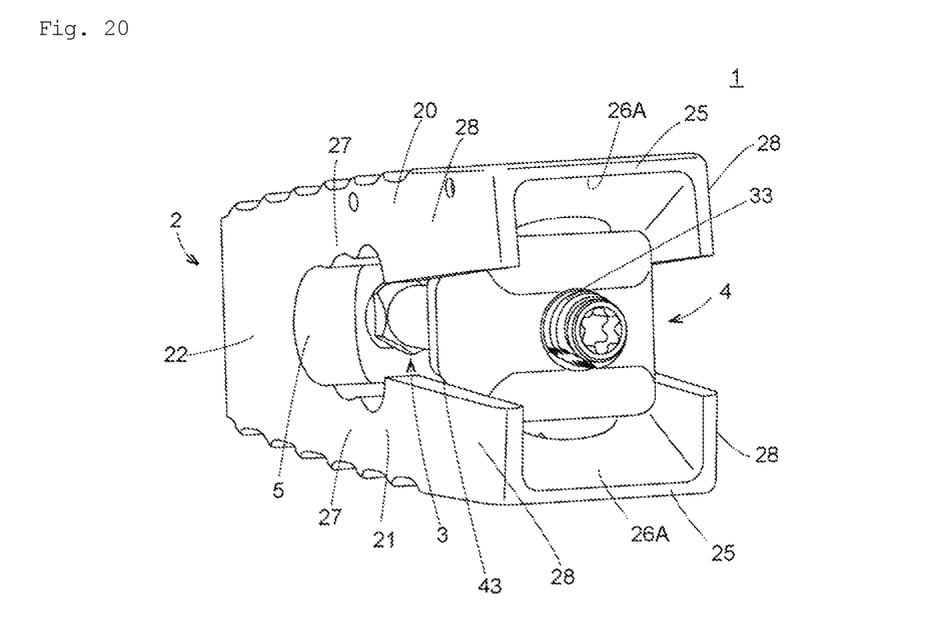
FIG. 20 is a perspective view of the expanded interbody cage.
Figure 21:
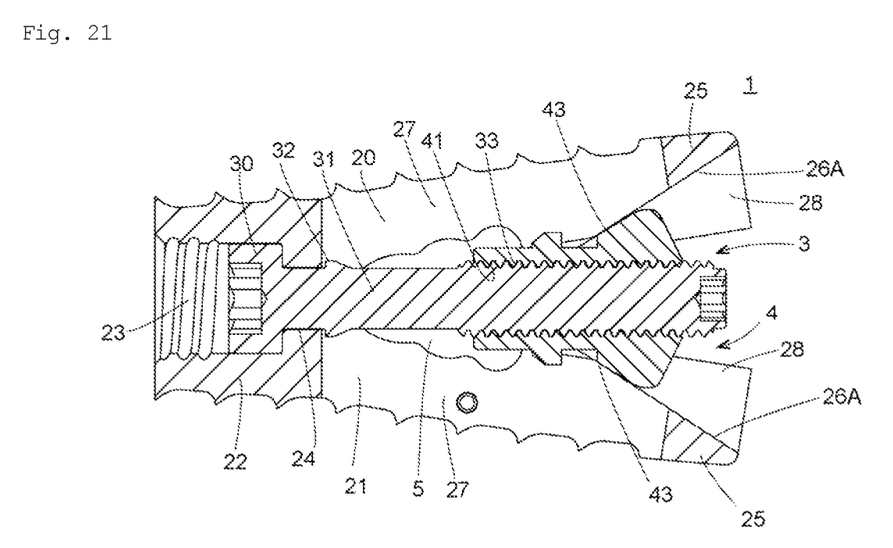
FIG. 21 is a cross-sectional view of the expanded interbody cage.

In the initial state before the interbody cage 1 expands, these two contact surfaces 43 are each partially in contact with at least part of the corresponding inclined surface 26A of the two branches 20,21 of the main body 2. As illustrated in FIGS. 20 and 21, when the slider 4 moves toward the rear end in the axis direction of the rod 3, each contact surface 43 slides on the corresponding inclined surface 26A. At this stage, each contact surface 43 pushes the corresponding inclined surface 26A upward or downward to deform the two branches 20,21 so that the branches 20,21 distally spread out one above the other. This causes the two branches 20,21 placed in parallel to each other to separate one above the other, thereby expanding the interbody cage 1. The lordosis angle of the spine varies from person to person, and depending on the site. Thus, an interbody can be reinforced with the interbody cage 1 in a condition suitable for a patient by adjusting the degree of expansion of the interbody cage 1 according to the height and angle between the vertebral bodies to which the interbody cage 1 is attached.

The slider 4 includes a pair of positioning protrusions 46 configured to regulate the movement of the slider 4 toward the distal end in the axis direction with respect to the rod 3 in the initial state before the interbody cage 1 expands. Each positioning protrusion 46 protrudes from the upper or lower plain surface 45 of the axis part 44. In the initial state before the interbody cage 1 expands, each positioning protrusion 46 hits the front end of the aperture edge that forms the orifice 53 of the two branches 20,21 of the main body 2 in the longitudinal direction, thereby defining the position of the slider 4 with respect to the main body 2, and regulating the movement of the slider 4 toward the distal end in the axis direction with respect to the rod 3.

Figure 1:
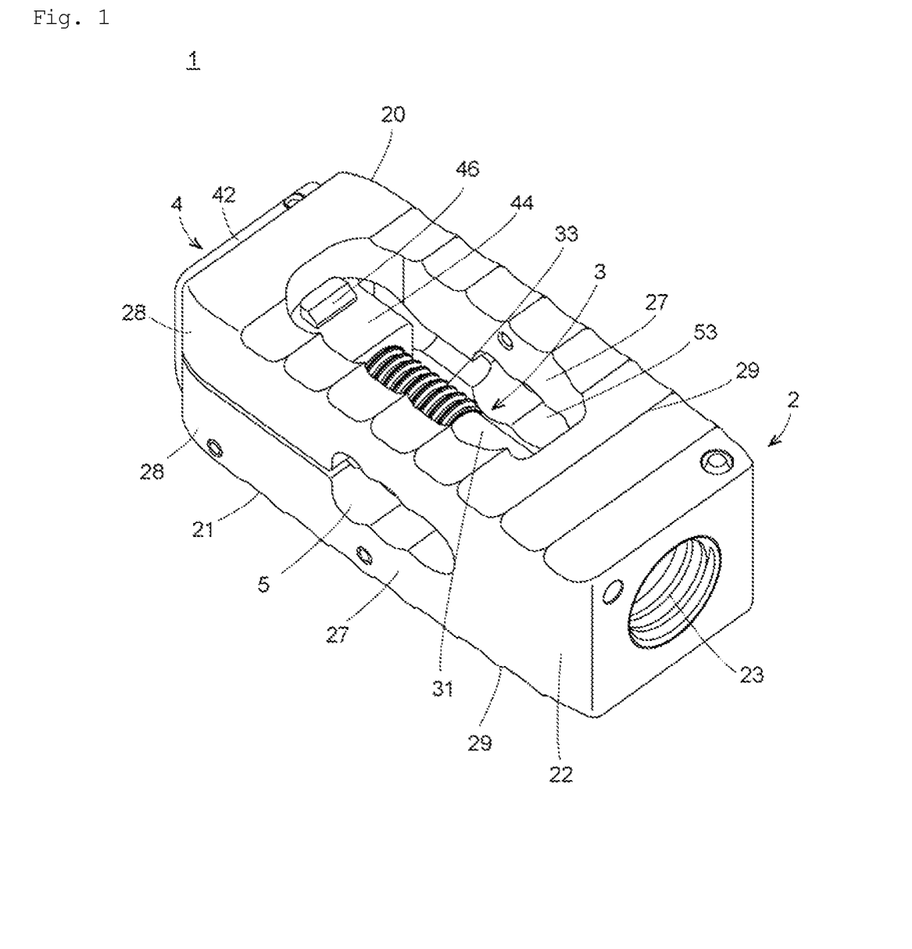
FIG. 1 is a perspective view of the interbody cage.
Figure 2:
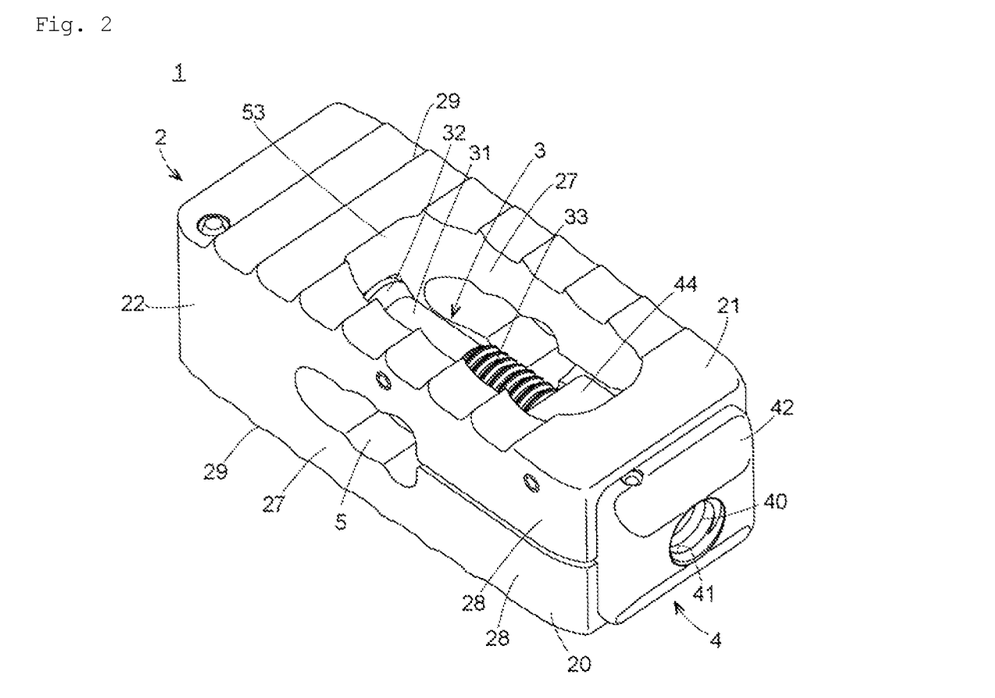
FIG. 2 is a perspective view of the interbody cage.
Figure 3:
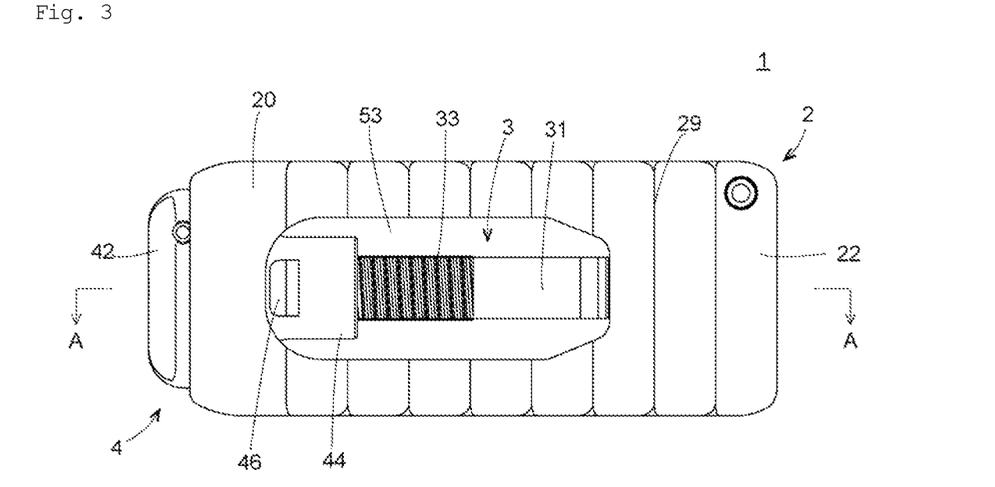
FIG. 3 is a plan view of the interbody cage.
Figure 4:
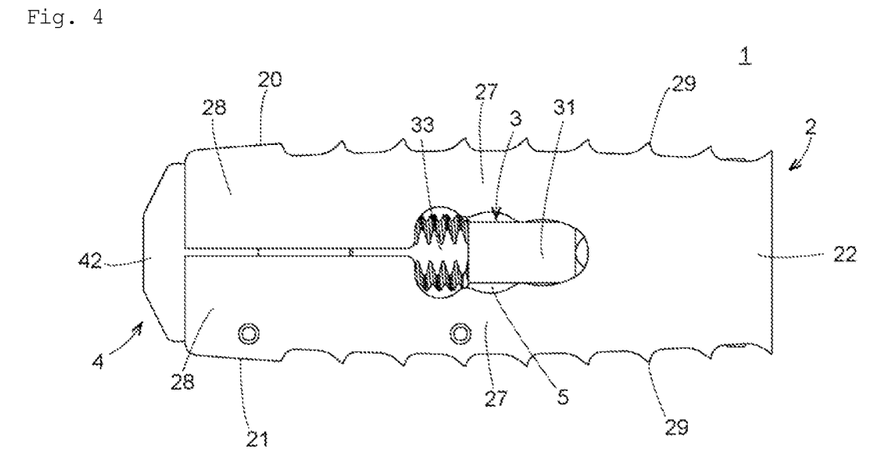
FIG. 4 is a lateral view of the interbody cage.
Figure 5:
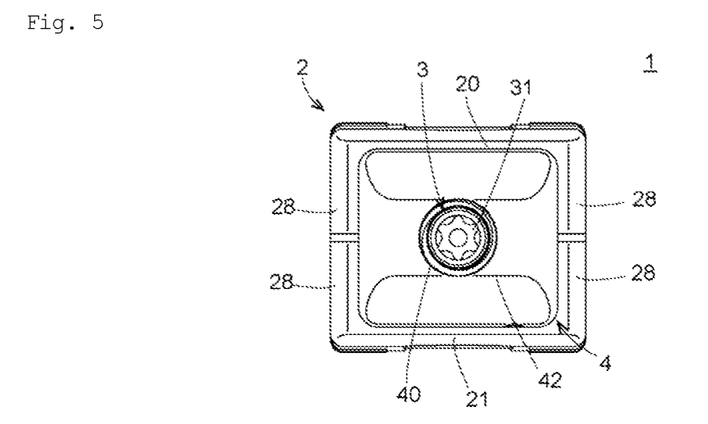
FIG. 5 is a front view of the interbody cage.
Figure 6:
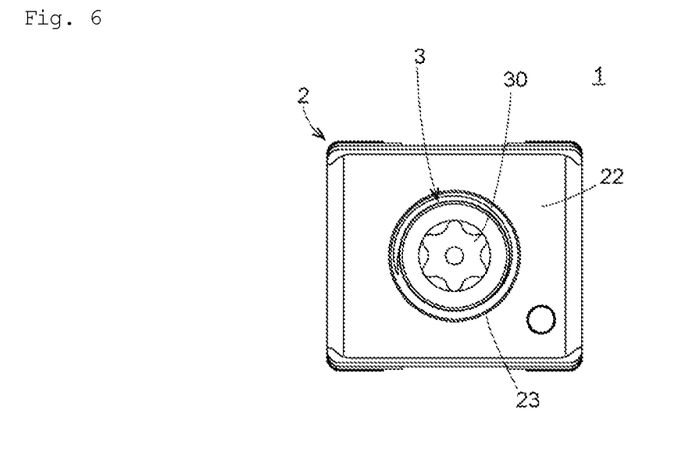
FIG. 6 is a rear view of the interbody cage.
Figure 7:
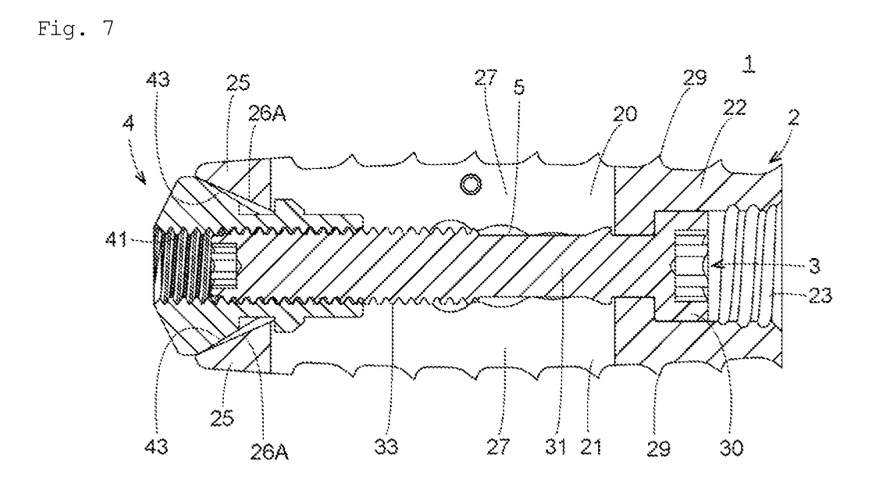
FIG. 7 is a vertical cross-sectional view of the interbody cage.
Figure 8:
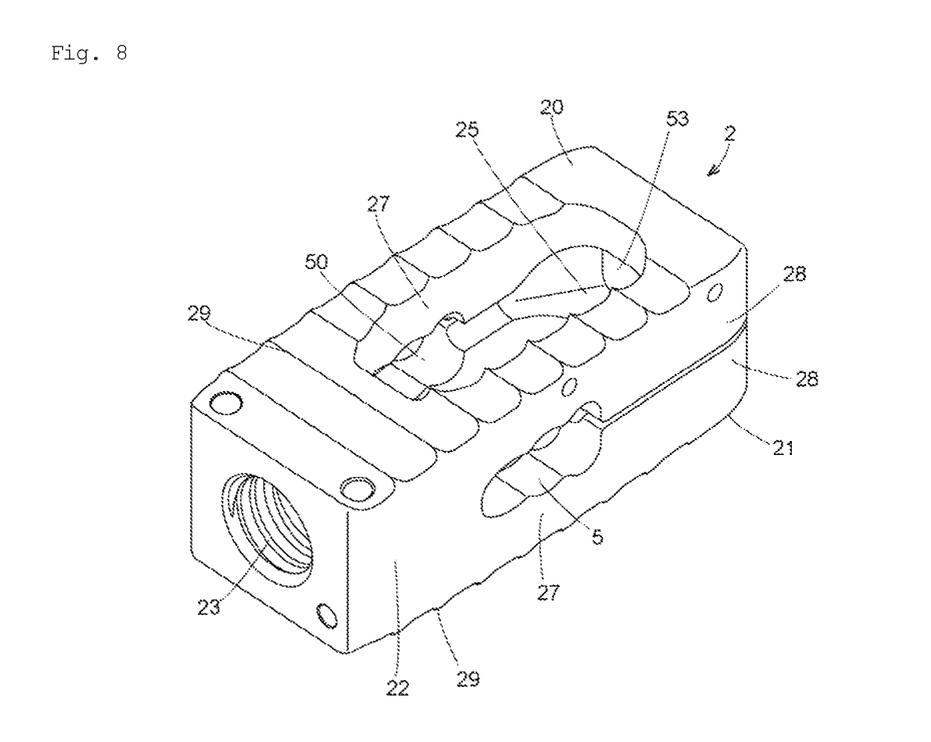
FIG. 8 is a perspective view of the main body.
Figure 9:
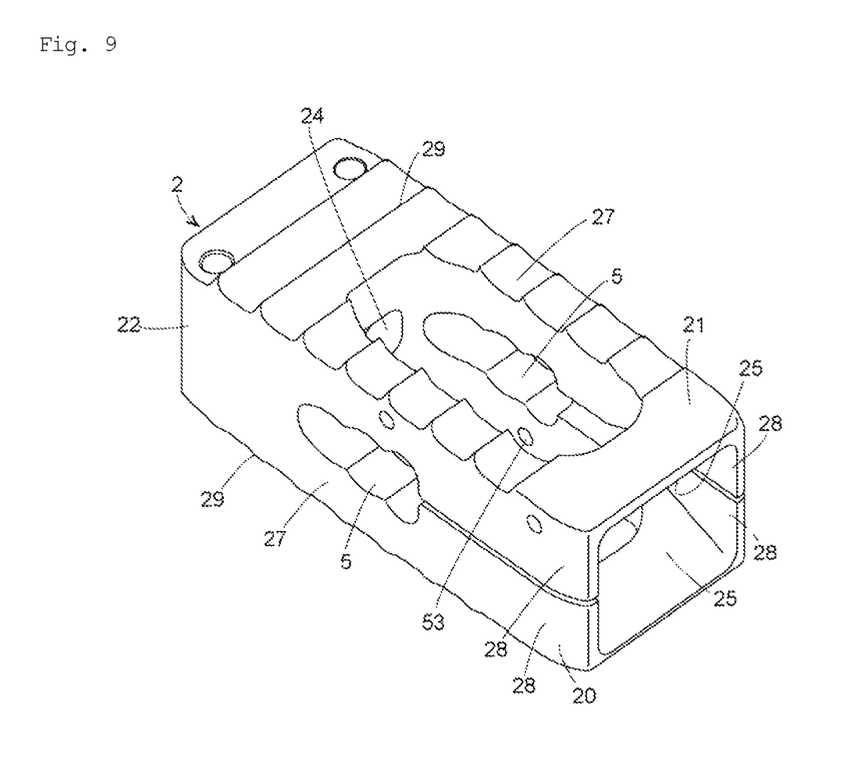
FIG. 9 is a perspective view of the main body.
Figure 10:
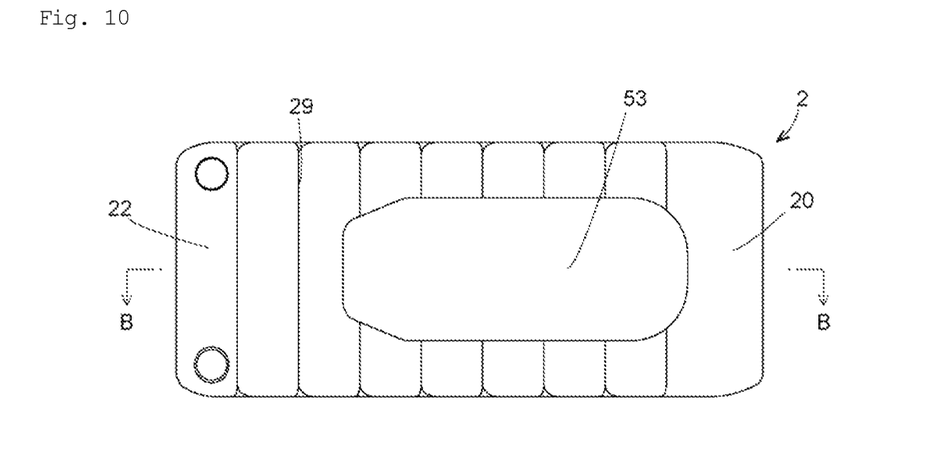
FIG. 10 is a plan view of the main body.
Figure 11:
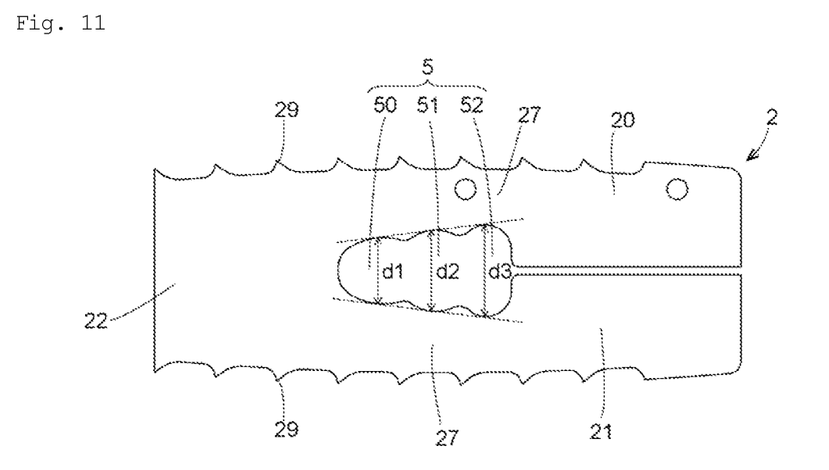
FIG. 11 is a lateral view of the main body.
Figure 12:
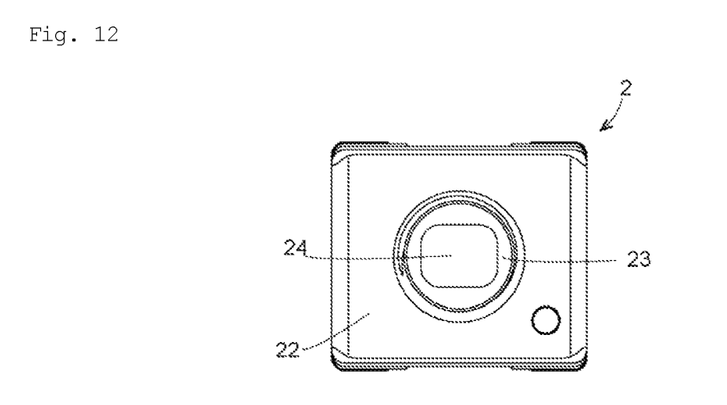
FIG. 12 is a rear view of the main body.
Figure 13:
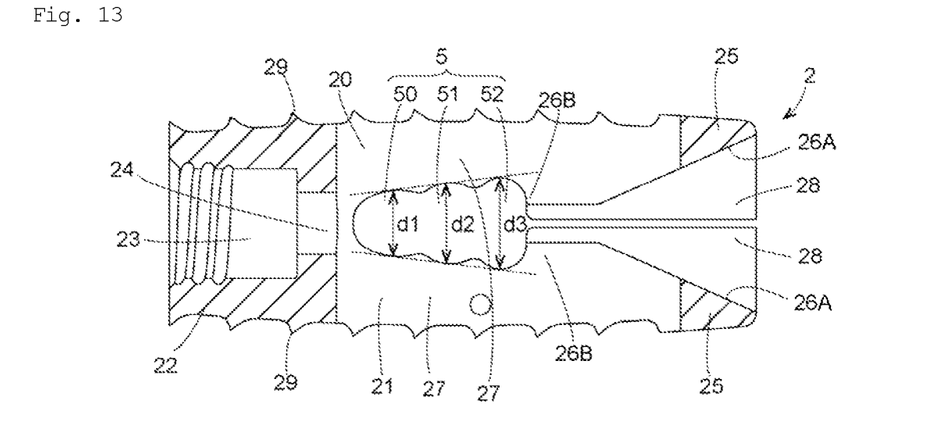
FIG. 13 is a cross-sectional view of the main body.

As illustrated in FIGS. 11 and 13, the vertical distance between the two branches 20,21 increases vertically from the proximal end position close to the base 22 of the main body 2 over a predetermined length, and the opening 5 that is larger in diameter in the vertical direction is proximally provided. Due to this opening 5, the two branches 20,21 of the main body 2 each include the constricted part 27 with a narrowed thickness on the base 22 side (proximal end side). The constricted parts 27 enable the two branches 20,21 to flexibly bend and deform when the two branches 20,21 deform so as to distally open upward and downward with the movement of the slider 4, and thus enable the two branches 20,21 to smoothly separate from each other in an effortless manner.

In this embodiment, the opening 5 is formed of a plurality of (three in this embodiment) holes 50,51,52 continuous in the longitudinal direction (in the axis direction of the rod 3). In a lateral view, the upper edge and the lower edge of the plurality of holes 50,51,52 form protruding curves; the protruding curves of the upper edge of adjacent holes 50 and 51 or 51 and 52 are smoothly connected and the protruding curves of the lower edge of adjacent holes 50 and 51 or 51 and 52 are smoothly connected. Thus, the opening 5 has a gourd shape between the upper and lower constricted parts 27 in a lateral view.

The protruding curves of the upper and lower edges of the plurality of holes 50,51,52 differ in radius of curvature. The radius of curvature is smaller toward the distal end of each branch 20,21. Specifically, of the plurality of holes 50,51,52, the radius of curvature of the first hole 50, which is on the most proximal side (rearmost) closest to the proximal end position, is the largest. The radius of curvature of the second hole 51 adjacent to the first hole 50 is the second largest. The radius of curvature of the third hole 52, which is on the most distal side (frontmost) far from the proximal end position, is the smallest. The upper edge and the lower edge of the first hole 50 are connected through a protruding curve whose radius of curvature is smaller than that of the protruding curves of the upper and lower edges of the first hole 50 on the side opposite the side adjacent to the second hole 51. In a lateral view, the first hole 50 has a substantially elliptical shape long in the axis direction of the rod 3 (a shape that forms part of an ellipse).

In this embodiment, the opening 5 is flared so as to expand upward and downward toward the front (the distal end) in a lateral view. Specifically, the holes 50,51,52 that constitute the opening 5 respectively have a diameter d1,d2,d3 that becomes larger toward the front. Of the plurality of holes 50,51,52, the top of the upper edge and the lower edge of the first hole 50, which is on the most proximal side, is the lowest. The top of the upper edge and the lower edge of the second hole 51, adjacent to the first hole 50, is the second lowest. The top of the upper edge and the lower edge of the third hole 52, which is on the most distal end side, is the highest.

When the two branches 20,21 are bent and deformed with the movement of the slider 4, a high stress is generated at the constricted part 27 of each branch 20,21. If stress concentration, which is a local increase in stress, occurs at the constricted parts 27, the constricted parts 27 become susceptible to breakage. This stress concentration is likely to occur at the portion near the proximal end position (base portion) of the opening 5. Thus, making the shape of the base portion round is effective in reducing the stress concentration at the base portion of the opening 5. In making the shape of the base portion of the opening 5 round, a larger radius of curvature is preferable because stress concentrates more as the radius of curvature is smaller; on the other hand, when the radius of curvature is overly large, with the base portion of the opening 5 having a circular shape in a lateral view, the base portion becomes too long in the vertical direction, making the constricted part 27 of each branch 20,21 thin and vulnerable, which results in a high stress.

Thus, in this embodiment, the outline of the first hole 50, which corresponds to the base portion of the opening 5, is made substantially elliptical and long in the axis direction of the rod 3 in a lateral view, thereby enabling the radius of curvature of the upper edge and lower edge of the base portion to increase without decreasing the thickness of the constricted part 27 of each branch 20,21. This can reduce the stress concentration at the base portion of the opening 5 and decrease the maximum stress generated at the constricted part 27 of each branch 20,21, thereby preventing the breakage of the constricted parts 27.

Additionally, extensive research of the present inventor confirmed that forming the opening 5 by connecting a plurality of holes 50,51,52 disperses stress that concentrates at the first hole 50, which corresponds to the base portion of the opening 5, into the adjacent second and third holes 51,52, and thereby reduces the stress concentration at the base portion of the opening 5. In this embodiment, the maximum stress generated at the constricted part 27 of each branch 20,21 can be more effectively decreased; thus, breakage of the constricted parts 27 can be prevented well. Also, due to the radius of curvature of the second and third holes 51,52 adjacent to the first hole 50 becoming gradually smaller, the stress, which is likely to concentrate at a hole with a smaller radius of curvature, is easily dispersed into the second and third holes 51,52. Thus, stress concentration at the first hole 50 is more effectively reduced.

Additionally, extensive research of the present inventor confirmed that due to the opening 5 having a flared shape that expands upward and downward toward the front, stress is easily dispersed into the second and third holes 51,52, adjacent to the first hole 50, and that stress is received substantially evenly by the holes 50,51,52. In this embodiment, the maximum stress generated at the constricted part 27 of each branch 20,21 can be more effectively decreased; thus, breakage of the constricted parts 27 can be better prevented.

The interbody cage 1 described above can be produced in various different sizes so as to be suitably adapted to patients.

Figure 22:
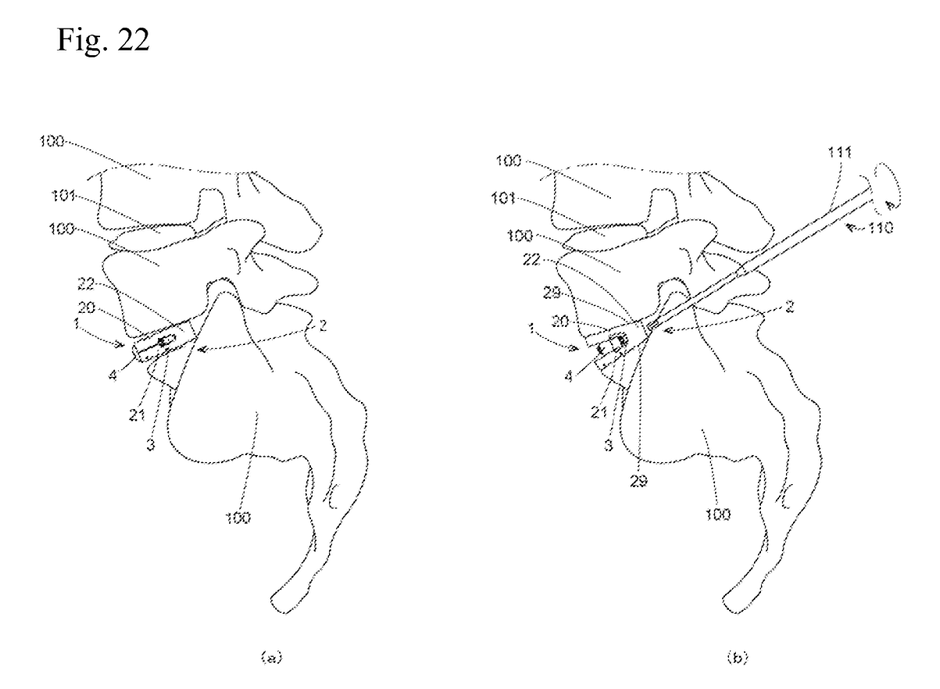
FIG. 22 illustrates the interbody cage attached in an interbody.

To attach the interbody cage 1 configured as described above in the space between the vertebral bodies of vertically adjacent two vertebra of the spine, as illustrated in FIG. 22, the upper and lower vertebral bodies 100 are fixed at a proper height and angle between the vertebral bodies with a pedicle screw system (not shown), and a degenerated intervertebral disc 101 and/or bone spurs are removed. In the space formed by removing the intervertebral disc 101 between the upper and lower vertebral bodies 100, the interbody cage 1 is inserted (FIG. 22(*a*)).

The rod 3 within the main body 2 is then rotated with a screwdriver 110 by remote control to separate the branches 20,21 of the main body 2 upward and downward. Specifically, the adapter at the extremity of the screwdriver 110 is fit into the head 30 of the rod 3, and a handle 111 is rotated to screw the external thread 33 of the rod 3 into the slider 4. This causes the slider 4 to move in the axis direction of the rod 3 toward the proximal end (on the base 22 side of the main body 2). During the movement of the slider 4, the contact surface 43 of the slider 4 slides on the inclined surface 26A of each branch 20,21 and causes each branch 20,21 to bend and deform upward or downward to separate from each other, thereby expanding the interbody cage 1 (FIG. 22(*b*)).

The interbody cage 1 is attached between the upper and lower vertebral bodies 100 by adjusting the degree of expansion of the interbody cage 1 in the following manner. The rotation of the rod 3 with the screwdriver 110 is controlled so that the outer surface of each branch 20,21 closely comes into contact with the upper or lower vertebral body 100 to allow the plurality of projections 29 to engage with the upper or lower vertebral body 100.

The interbody cage 1 according to this embodiment can expand upward and downward and maintain a normal height and angle between vertebral bodies by properly adjusting the degree of expansion according to the patient. Thus, the interbody cage 1 enables correction of the spine suitable for the patient (recovery and acquisition of the lordosis angle). Additionally, the interbody cage 1 reliably reinforces the interbody, and prevents the interbody from being squished due to pressure applied from the upper and lower vertebral bodies 100; thus, the interbody cage 1 can also prevent delayed bone fusion and nonunion.

When each branch 20,21 is bent and deformed with the movement of the slider 4, a high stress is generated at the constricted part 27 of each branch 20,21. However, due to the opening 5 formed by connecting a plurality of holes 50,51,52 whose upper edge and lower edge form protruding curves, the interbody cage 1 according to this embodiment can disperse the stress that concentrates at the first hole 50, which corresponds to the base portion of the opening 5, into the adjacent second and third holes 51,52, thereby reducing stress concentration at the base portion of the opening 5. Because the opening 5 enables the interbody cage 1 to prevent stress concentration, which is a local increase in stress at the constricted parts 27, and thus prevent well the breakage of the constricted parts 27, the opening 5 can make the interbody cage 1 more structurally stable.

The interbody cage 1 according to this embodiment can more effectively reduce the stress concentration at the base portion of the opening 5 due to each of the following: (1) the rearmost hole 50 among the plurality of holes 50,51,52 has a shape that is part of an ellipse long in the axis direction of the rod 3 in a lateral view; (2) the radius of curvature of the protruding curves of the upper edge and lower edge of the plurality of holes 50,51,52 becomes smaller toward the front; and (3) the opening 5 is flared so as to expand upward and downward toward the front. Thus, the interbody cage 1 can better prevent the breakage of the constricted parts 27.

In the interbody cage 1 according to this embodiment, When the branches 20,21 of the main body 2 are separate one above the other, the branches 20,21 are separately supported by each contact surface 43 of the slider 4 that lies between the branches 20,21. In order to stably maintain the space between the vertebral bodies in a near-normal condition, the interbody cage is required to be structurally stable so as to enable each branch 20,21 to maintain the space between the vertebral bodies without lowering their performance or deforming even if the branches 20,21 receive pressure from the upper and lower vertebral bodies due to changes in body weight or posture. If the slider 4 is cylindrical, as in the interbody cage of PTL 1, the slider 4 comes in line-to-line contact with the inclined surface 26A of each branch 20,21; the area in which the slider 4 is in contact with the inclined surface 26A becomes small. Thus, when the branches 20,21 receive pressure from the upper and lower vertebral bodies after implantation, stress concentrates at the constricted parts 27 at the root portion, which may break the constricted parts 27. In contrast, when the branches 20,21 receive pressure from the upper and lower vertebral bodies after implantation in the interbody cage 1 according to this embodiment, the inclined surface 26A of each branch 20,21 comes in surface-to-surface contact with the corresponding contact surface 43 of the slider 4; the area in which the slider 4 is in contact with the inclined surface 26A becomes large. Thus, even if the branches 20,21 receive pressure from the upper and lower vertebral bodies while the interbody cage 1 reinforces the space between the vertebral bodies, the slider 4 supporting each branch 20,21 on the surface thereof can reduce the stress concentration at the constricted part 27 at the root portion of each branch 20,21, and thereby prevent the breakage of the constricted parts 27. Accordingly, the structurally stable interbody cage 1 can be provided.

Additionally, because the main body 2 and the slider 4 of the interbody cage 1 according to this embodiment are formed from polyether ether ketone (PEEK), bone union can be visually confirmed well in diagnostic imaging after surgery. PEEK also has an elasticity (hardness) substantially equivalent to that of bone. Thus, when the interbody cage 1 receives pressure from the upper and lower vertebral bodies with the interbody cage 1 attached between the vertebral bodies, the use of PEEK can prevent the interbody cage 1 from sinking into the vertebral bodies, and compressing nerves. Moreover, because the branches 20,21 of the main body 2 easily bend and deform, the branches 20,21 can be smoothly opened one above the other by the movement of the slider 4, without the need to overly decrease the thickness of the constricted parts 27.

The above describes the interbody cage 1 according to an embodiment of the present invention. However, the present invention is not limited the above embodiment, and various modifications can be made without departing from the spirit and principal concept of the invention.

For example, although the opening 5 of the interbody cage 1 according to the above embodiment is flared so as to expand upward and downward toward the front, with the diameter d1,d2,d3 of the holes 50,51,52 that constitute the opening 5 becoming larger toward the front, the opening 5 does not necessarily have to be flared, and the diameter d1,d2,d3 of the holes 50,51,52 that constitute the opening 5 may be identical.

Although the radius of curvature of the protruding curves of the upper edge and the lower edge of the plurality of holes 50,51,52 that constitute the opening 5 in the interbody cage 1 according to the above embodiment becomes smaller toward the front, the radius of curvature does not necessarily have to be smaller toward the front. The protruding curves of the upper edge and the lower edge of the plurality of holes 50,51,52 may all vary in radius of curvature, for example, with some having a large radius of curvature and the other having a small radius of curvature; or they may all have an identical radius of curvature.

Although the rearmost hole 50 among the plurality of holes 50,51,52 that constitute the opening 5 in the interbody cage 1 according to the above embodiment has a shape that is part of an ellipse (substantially elliptical shape) long in the axis direction of the rod 3 in a lateral view, the rearmost hole 50 does not necessarily have to have a substantially elliptical shape, and may have a substantially circular shape.

Although the interbody cage 1 according to the above embodiment uses a lead screw to translate the turning motion of the rod 3 into the linear motion of the slider 4 in order to move the slider 4 in the axis direction of the rod 3, the mechanism for moving the slider 4 in the axis direction of the rod 3 is not limited to the lead screw, and various known mechanisms can be applied.

Although the outer surface of the branch 20 and the outer surface of the branch 21 of the main body 2 in the interbody cage 1 according to the above embodiment are substantially parallel to each other, the outer surface of each branch 20,21 may be inclined toward the extremity such that the outer surfaces are gradually separate from each other; the outer surfaces of the branches 20,21 may form an open V shape when the interbody cage 1 is not expanded.

Although the slider 4 of the interbody cage 1 according to the above embodiment includes two contact surfaces 43 that individually correspond to the respective inclined surfaces 26A of the two branches 20,21 of the main body 2, the slider 4 does not necessarily have to include the contact surfaces 43. For example, the slider 4 may be formed in a cylindrical shape.

DESCRIPTION OF THE REFERENCE NUMERALS

1 interbody cage
2 main body
3 rod
4 slider
5 opening
20 branch
21 branch
26A inclined surface
43 contact surface
50 first hole
51 second hole
52 third hole

The invention claimed is:

1. An interbody cage configured to be attached between adjacent vertebral bodies of a spine, the interbody cage comprising
a main body distally including a pair of branches, the branches being spaced apart from each other upward and downward,
a rod provided in the main body so as to extend between the two branches, and
a slider configured to separate the two branches upward and downward, the slider being supported by the rod so as to be movable in an axis direction of the rod, wherein
the two branches each distally have an inclined surface, the inclined surfaces facing each other, a distance between the inclined surfaces gradually increasing toward distal ends thereof,
the slider slides on the inclined surfaces of the two branches when the slider moves in the axis direction of the rod, and
the two branches each have a constricted part with a narrow thickness present more proximally than the inclined surfaces, and an opening is present between an upper constricted part and a lower constricted part, the opening being formed of a plurality of holes continuous in the axis direction of the rod and having an upper edge and lower edge that form protruding curves in a lateral view.

2. The interbody cage according to claim 1, wherein the slider includes two contact surfaces that individually correspond to the respective inclined surfaces of the two branches, and each contact surface slides on the corresponding inclined surface when the slider moves in the axis direction of the rod.

3. The interbody cage according to claim 2, wherein each contact surface comes in surface-to-surface contact with the corresponding inclined surface when the two branches receive pressure from the upper and lower vertebral bodies.

4. The interbody cage according to claim 1, wherein a most proximal hole among the plurality of holes has a shape that is part of an ellipse long in the axis direction of the rod.

5. The interbody cage according to claim 1, wherein the protruding curves of the plurality of holes have a radius of curvature that is smaller toward the distal end.

6. The interbody cage according to claim 1, wherein the opening is flared so as to expand upward and downward toward the distal end in a lateral view.

7. The interbody cage according to claim 1, wherein the main body and the slider are formed from a biocompatible material.

* * * * *